(12) United States Patent
Isch et al.

(10) Patent No.: US 11,654,009 B2
(45) Date of Patent: *May 23, 2023

(54) HELICAL HOLLOW STRAND URETERAL STENT

(71) Applicant: Cook Medical Technologies LLC, Bloomington, IN (US)

(72) Inventors: Andrew P. Isch, West Lafayette, IN (US); Benjamin T. Biltz, Spencer, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 708 days.

This patent is subject to a terminal disclaimer.

(21) Appl. No.: 16/721,101

(22) Filed: Dec. 19, 2019

(65) Prior Publication Data

US 2020/0121443 A1 Apr. 23, 2020

Related U.S. Application Data

(63) Continuation of application No. 15/359,830, filed on Nov. 23, 2016, now Pat. No. 10,517,710.

(Continued)

(51) Int. Cl.
*A61F 2/04* (2013.01)
*A61F 2/852* (2013.01)
(Continued)

(52) U.S. Cl.
CPC .............. *A61F 2/04* (2013.01); *A61F 2/852* (2013.01); *A61F 2/88* (2013.01); *A61M 27/008* (2013.01);
(Continued)

(58) Field of Classification Search
CPC ...... A61F 2002/048; A61F 2/04; A61F 2/852; A61F 2/88; A61F 2/94; A61F 2210/0076; A61F 2/06; A61M 27/008; A61M 1/00
(Continued)

(56) References Cited

U.S. PATENT DOCUMENTS

| 5,015,253 A | 5/1991 | MacGregor |
| 5,772,668 A | 6/1998 | Summers |

(Continued)

FOREIGN PATENT DOCUMENTS

| FR | 2 661 604 | 5/1990 |
| WO | 2004/041345 A1 | 5/2004 |

OTHER PUBLICATIONS

Extended European Search for related EPO application No. 16201814.7, dated Mar. 7, 2017, 7 pp.
(Continued)

*Primary Examiner* — Yashita Sharma
(74) *Attorney, Agent, or Firm* — Crowell & Moring LLP

(57) ABSTRACT

A stent is provided that includes a body extending between a distal and a proximal end. The body is defined by a plurality of elongated members, with each elongated member extending between a distal end that is coterminous with the distal end of the body and a proximal end that is coterminous with the proximal end of the body. Each of the plurality of elongated members are arranged so as to define a lumen extending along the length of the respective plurality of elongated members, the lumen extending between the distal and proximal ends of the body so as to form a lumen length. Each of the plurality of elongated members are configured to permit drainage of a fluid from within the lumen to an environment external the stent along the entire lumen length.

5 Claims, 3 Drawing Sheets

Related U.S. Application Data

(60) Provisional application No. 62/262,634, filed on Dec. 3, 2015.

(51) Int. Cl.
*A61F 2/88* (2006.01)
*A61M 27/00* (2006.01)
*A61F 2/94* (2013.01)

(52) U.S. Cl.
CPC ........... *A61F 2/94* (2013.01); *A61F 2002/048* (2013.01); *A61F 2210/0076* (2013.01)

(58) Field of Classification Search
USPC ................................... 623/1.1–3.1; 604/326
See application file for complete search history.

(56) References Cited

U.S. PATENT DOCUMENTS

| | | |
|---|---|---|
| 8,192,500 B2 | 6/2012 | Chung |
| 8,394,138 B2 | 3/2013 | Melsheimer |
| 2004/0093076 A1 | 5/2004 | White et al. |
| 2008/0004578 A1 | 1/2008 | Hixon |
| 2008/0300665 A1 | 12/2008 | Lootz et al. |
| 2013/0053766 A1 | 2/2013 | Hollett |

OTHER PUBLICATIONS

"HHS® Tube helical hollow strand", this brochure is believed to have been known in the U.S. prior to the filing date of the application entitled "Helical Hollow Strand Ureteral Stent".

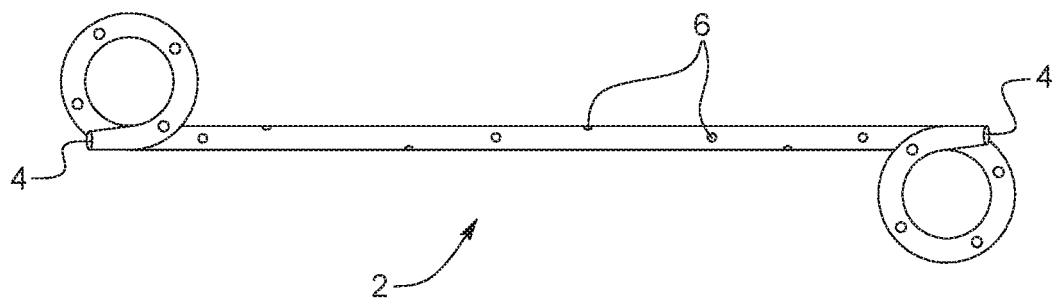
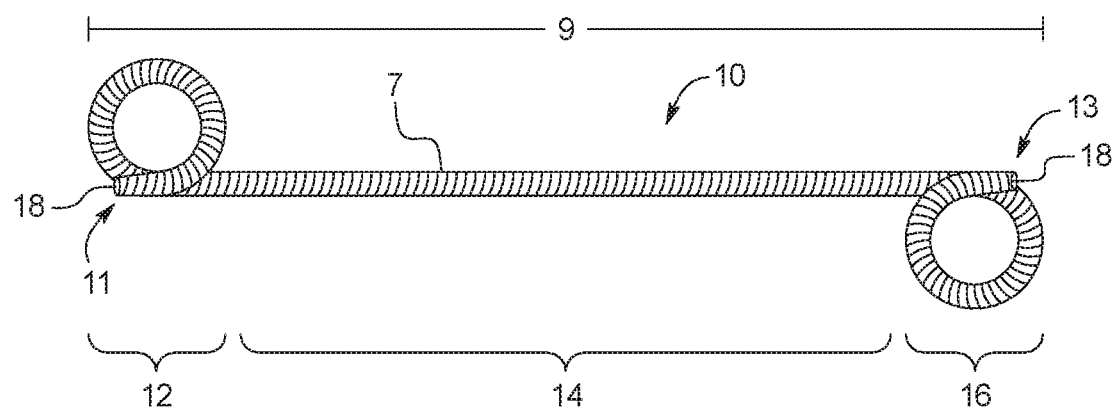

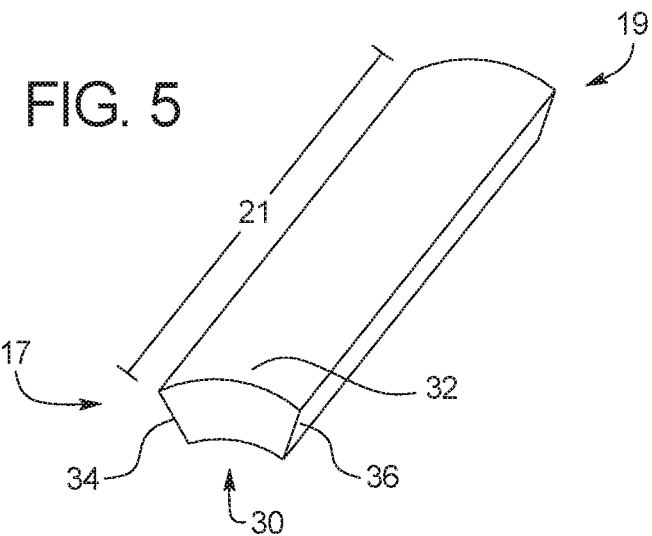
FIG. 5
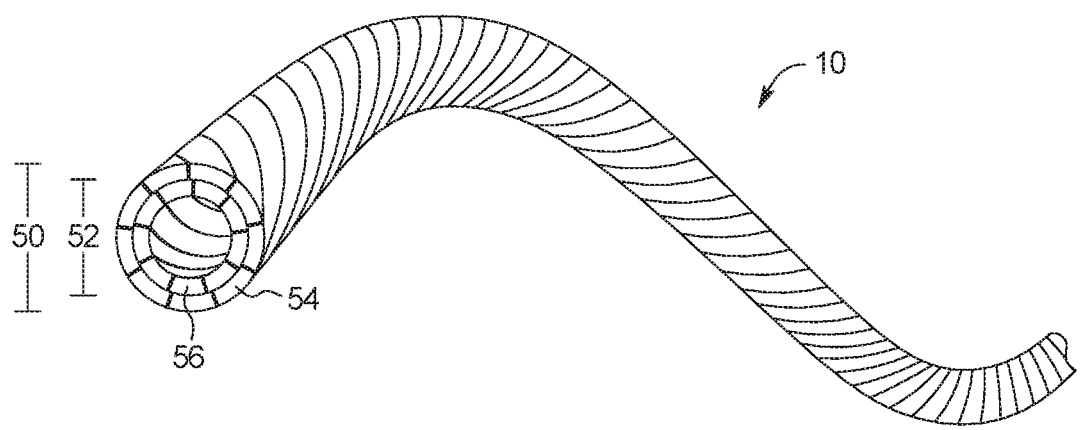
FIG. 6
FIG. 7A
FIG. 7B

HELICAL HOLLOW STRAND URETERAL STENT

CROSS-REFERENCE TO RELATED APPLICATIONS

The present patent application is a continuation of U.S. application Ser. No. 15/359,830, filed Nov. 23, 2016, issuing as U.S. Pat. No. 10,517,710 on Dec. 31, 2019, which claim the benefit of priority to U.S. Provisional U.S. Patent Application Ser. No. 62/262,634, filed Dec. 3, 2015, the entirety of each are hereby incorporated by reference.

FIELD

The present disclosure relates to medical devices and more specifically to stents.

BACKGROUND

The statements in this section merely provide background information related to the present disclosure and may not constitute prior art.

A stent is a tubular device that is placed into a body lumen, such as a blood vessel, of a patient to for example provide support to a weakened area or to maintain patency of a lumen within the body. Ureteral stents are a specific type of stents that are optimized for use in a patient's ureter. A ureteral, or ureteric, stent may be used to support a weakened ureter due to a variety of complications or to reopen a ureter that has been obstructed by a kidney stone.

The majority of ureteral stents used today are flexible polymer tubes that include drainage side ports and loops at each end (FIG. 1). A guide wire is inserted into the patient's ureter and the stent is delivered over the guide wire and positioned within the patient's ureter. Polymer ureteral stents are designed to be flexible to reduce patient discomfort. However, polymer ureteral stents have several drawbacks. First, polymers degrade at a greater rate than other biocompatible materials and therefore they are only approved to be used for a short period of time (e.g. 6 months) before they must be removed from the patient and replaced. Second, polymers have a high surface friction, thus necessitating the use of a hydrophilic coating to prevent unwanted friction between the stent and the ureteral wall to prevent or limit damage to the ureteral wall. Third, polymer stents have low radial strength, meaning they are unsuitable for use in patients where a high radial strength is necessary to properly support the ureteral wall. Fourth, because the polymer stents are designed to be flexible, tensile strength and torqueability is sacrificed, which may result in insufficient support of the ureteral wall.

Thus, it is desirable to provide a ureteral stent with high tensile, torque, compressive, and radial strength while maintaining maximum flexibility for patient comfort. Additionally, it is desirable to provide a ureteral stent that allows for passage over a guide wire and may remain indwelled in a patient for a long period of time.

SUMMARY

In one form of the present disclosure, a stent is provided. The stent comprises a body extending between a distal end and a proximal end. The body is defined by a plurality of elongated members, each elongated member extending between a distal end that is coterminous with the distal end of the body and a proximal end that is coterminous with the proximal end of the body. Further, each of the plurality of elongated members are arranged so as to define a lumen extending along the length of the respective plurality of elongated members, the lumen extending between the distal and proximal ends of the body so as to form a lumen length. Also, each of the plurality of elongated members are configured to permit drainage of a fluid from within the lumen to an environment external the stent along the entire lumen length.

Further, the stent may have each of the plurality of elongated members extend in a helical pattern to define a surface of the body and the lumen. The stent may also include the plurality of elongate members comprising a first plurality of elongated members and a second plurality of elongated members, wherein the first plurality of elongated members form an inner layer to define the lumen, and the second plurality of elongated members form an outer layer that surrounds the inner layer. The first plurality of elongated members may extend around and along the lumen in a clockwise helical pattern while the second plurality of elongated members may extend around and along the lumen in a counterclockwise helical pattern. The lumen may also be configured so as to allow the passage of a wire guide therethrough. The stent may further comprise a distal portion, a proximal portion, and a central portion, wherein one or both of the distal and proximal end portions are biased into a shape other than straight.

In another form of the present disclosure, a method for placing a ureteral stent is provided. This method comprises providing a stent that comprises a body extending between a distal end and a proximal end. The body is defined by a plurality of elongated members, each elongated member extending between a distal end that is coterminous with the distal end of the body and a proximal end that is coterminous with the proximal end of the body. Further, each of the plurality of elongated members are arranged so as to define a lumen extending along the length of the plurality of elongated members, the lumen extending between the distal and proximal ends of the body so as to form a lumen length. Also, each of the plurality of elongated members are configured to permit drainage of a fluid from within the lumen to an environment external the stent along the entire lumen length. The method further comprises advancing the ureteral stent into a ureter of a patient until the ureteral stent is positioned within the ureter.

The method may also comprise advancing a guide wire into the ureter before the step of advancing the ureteral stent into the ureter wherein the step of advancing the ureteral stent into the ureter further comprising advancing the ureteral stent over the guide wire. The method may also comprise removing the guide wire from the ureter. Additionally, the method may include removing the ureteral stent from the ureter.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1 is a side view of a known ureteral stent design;

FIG. 2 is a side view of a ureteral stent constructed in accordance with the teachings of the present disclosure;

FIG. 5 is an orthogonal view of a filar of a ureteral stent;

FIG. 6 is a cross-sectional view of one example of a ureteral stent;

FIG. 7A is a cross-sectional view of an inner filar of a ureteral stent; and

FIG. 7B is a cross-sectional view of an outer filar of a ureteral stent.

DETAILED DESCRIPTION

Figure 3:
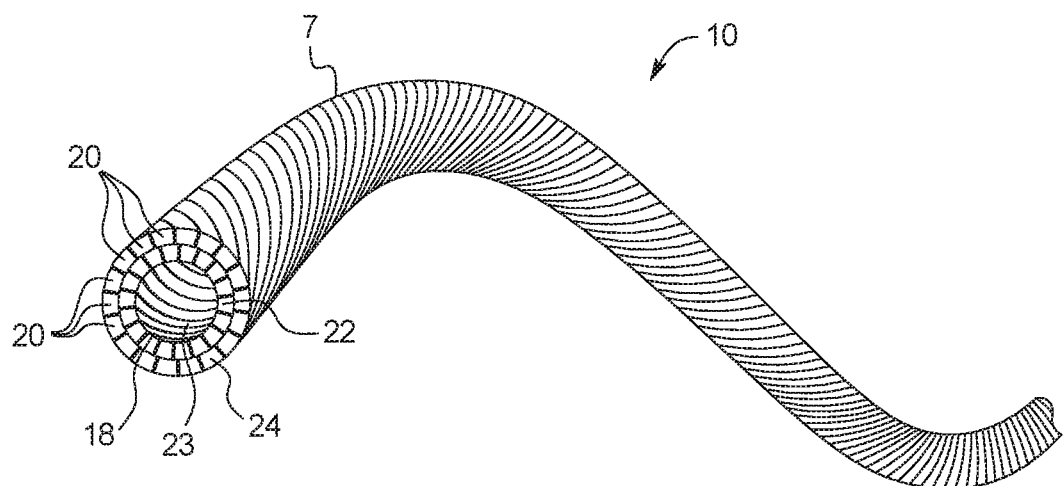
FIG. 3 is a cross-sectional view of a ureteral stent.

The following description is merely exemplary in nature and is not intended to limit the present disclosure, application, or uses. It should be understood that throughout the drawings, corresponding reference numerals indicate like or corresponding parts and features. It should also be understood that various cross-hatching patterns used in the drawings are not intended to limit the specific materials that may be employed with the present disclosure. The cross-hatching patterns are merely exemplary of preferable materials or are used to distinguish between adjacent or mating components illustrated within the drawings for purposes of clarity.

Referring to FIG. 2, a ureteral stent 10 is provided. The ureteral stent 10 may have a body 7 with a distal end 11, and proximal end 13, a distal portion 12, central portion 14, and proximal portion 16. The ureteral stent 10 may further include a lumen 18 that extends through the entire length 9 of the stent 10. As can be seen, the central portion 14 of the ureteral stent 10 may be substantially straight along the entire length thereof. In contrast, one or both the distal portion 12 and proximal portion 16 may be straight or biased into loops, pigtails, or any other shape other than straight. The loops or other shapes may be formed by mechanical or plastic deformation or by heat setting the metal formed around a jig. The loops or other shapes may allow urine to travel through the center lumen as well as the sidewalls.

Figure 4:
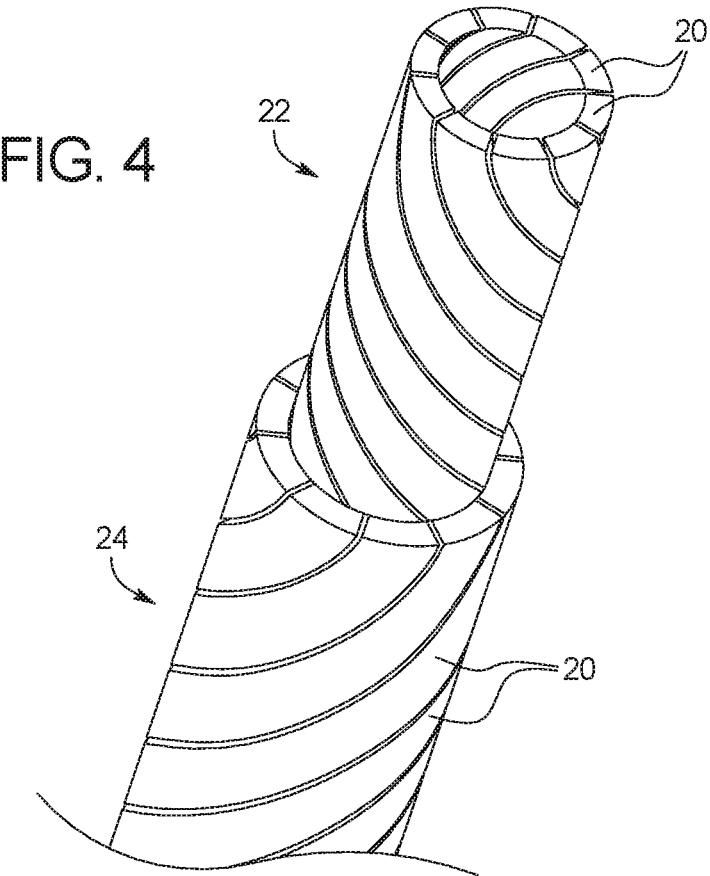
FIG. 4 is an exemplary schematic of a ureteral stent with two layers of filars.

FIG. 3 shows a cross-section view of the ureteral stent 10. As can be seen, the body 7 of the ureteral stent 10 may be defined by a plurality of thin, elongated members, or filars 20, that each extend between a distal end that is coterminous with the distal end 11 of the body 7 and a proximal end that is coterminous with the proximal end 13 of the body 7. The filars 20 need not extend completely from the distal end 11 to the proximal end 13 of the body 7 to be considered coterminous, as long as the filars 20 extend a substantial portion of that distance. Each of the plurality of elongated members are arranged to form and define a lumen 18. The lumen 18 may extend along the entire length 9 of the stent 10: from the proximal end 13 to the distal end 11. Alternatively, the lumen 18 may extend along only a portion of the length 9 of the stent 10. Each filar 20 may have a proximal end 17 and a distal end 19 (FIG. 5). The filars 20 may each include a length 21 (FIG. 5) along which the filars 20 are aligned so as to form the tube. As shown in FIG. 3, the filars 20 may be wound in a helical pattern along the lengths 21 of the filars 20 and around the lumen 18. The filars 20 may extend around and along the lumen 18 at varying pitch magnitudes, including a pitch magnitude that allows for multiple helical revolutions around the lumen 18 between the distal end 11 and the proximal end 13 of the body 7. In one non-limiting example, the pitch may range from 50-200 threads per inch. Alternatively, the filars 20 may extend straight along their entire lengths 21, or in some other common pattern. The present embodiment also has two separate layers of filars 20: an inner layer 22 and an outer layer 24. The inner layer 22 may define the lumen 18 and the surface 23 of the lumen 18, while the outer layer 24 surrounds the inner layer 22. The filars 20 of both the inner and outer layers may be wound helically in the same direction along their lengths 21 (i.e. clockwise or counter-clockwise). Alternatively, the filars 20 of the inner layer 22 may be wound helically in a clockwise direction along their lengths 21 while the outer layer 24 of the filars 20 may be wound helically in a counterclockwise direction, or vice versa. FIG. 4 shows an exemplary stent 10 with a portion of the outer layer 22 removed so as to clearly show the inner layer 22 and outer layer 24 where the filars 20 are wound in opposite helical directions. FIG. 4 is merely a schematic, and the stent 10 may have different numbers of filars 20 per layer, including a different number of filars 20 for each layer. The inner layer 22 filars 20 may extend around and along the lumen 18 at the same or varying pitch magnitudes as the outer layer 24 filars 20. To prevent the filars 20 from unwinding and separating, the ends of the filars 20 may be bonded, soldered, welded, or otherwise mechanically or chemically attached together. Additionally, the ends of the filars 20 may be electropolished or otherwise finished to provide a smooth end of the stent 10 to ease introduction of the stent 10 into the patient. Alternative means of securing the ends or any other portion of the filars 20 together may be used. Additionally, the filars 20 may be bonded together at various locations along the lengths 21 of the filars 20. Optionally, one or both ends of the stent 10 may be tapered, so as to ease introduction of the stent 10 into the patient. For example, the stent 10 with two layers 22, 24 of filars 20 may be tapered and then welded together at the end of the stent 10 to form a smooth, rounded end. The end may then be electropolished to ensure a smooth end of the stent 10.

While the embodiment shown in FIG. 3 includes two layers 22, 24 of filars 20, any number of layers is contemplated, including a single layer or three or more layers of filars 20. Additionally, the embodiment in FIG. 3 includes 18 individual filars 20 for each of the inner and outer layers 22, 24 for a total of 36 filars 20. However, any number of filars 20 may be used, including a different number of filars 20 for each layer. Further, the diameter of the lumen 18, or inner diameter, and the outside diameter of the stent 10, may be varied as desired by altering the size and number of filars 20. The design of the filars 20 may be varied as well. The filars 20 may have varying cross-sections, such as circular or rectangular. However, the filars 20 in this embodiment have a cross-section as shown in FIG. 5. Each filar 20 in this embodiment may include an inner surface 30, an outer surface 32, and two side surfaces 34, 36. The inner surface 30 may have a curved concave shape such that when the filars 20 are arranged together, a smooth, circular inner surface is provided to form the lumen 18. Similarly, the outer surface 32 may have a curved, convex shape such that when the filars 20 are wound together, a smooth, cylindrical outer surface is provided along the entire length 9 of the stent 10.

The filars 20 may be made of a variety of biocompatible materials. Ideally, due to its strength properties and resilience, a biocompatible metal may be used. However, the filars 20 may be made of other materials such as polymers. Other material examples for the filars 20 include, but are not limited to: nitinol, cobalt chrome alloys, 35N LT, MP35N, 304V and 304LV stainless, L605, FWM 1058, FWM 1537, Titanium Ti6Al-4V ELI, or any other material with a high corrosion resistance.

As shown in FIG. 1, typical ureteral stents include drainage ports 6 along the length of the stent 2. These drainage ports 6 provide fluid communication between the lumen 4 of the stent 2 and an environment external the stent 2. Ureteral stents must provide drainage along a substantial length of the stent due to blockages that may form in the lumen due to encrustation or biofilm formation. Due to the composition of urine, calcifications may form around the ureteral stent which can cause obstructions and potentially infection. Including drainage ports along the entire length of the stent limits the possibility that the stent may become entirely obstructed. In contrast to the ureteral stent 2 shown in FIG. 1, the ureteral stent 10 shown in FIGS. 2 and 3 does not include any drainage ports. Drainage ports are not necessary in the present design because the filars 20 may be designed and arranged in such a way so as to allow drainage through the side walls of the inner and outer layers along a portion of the length of the stent (such as the central portion, for example), or along the entire length 9 of the stent 10. When designed properly, small, imperceptible gaps exist between neighboring filars 20 that are large enough to allow a fluid to flow from the lumen 18, through these gaps, and into an environment external to the stent 10 along the entire length 9 of the stent 10, or a portion of the length of the stent 10. While many factors may affect the rate at which the fluid may drain from the lumen 18 to an environment external the stent 10, research has shown that altering the shape of the individual filars 20 so as to provide larger gaps along the lengths 21 of the filars 20 may increase the drainage rate. Additionally, reducing the number of filar layers may also increase the drainage rate. However, one of ordinary skill in the art upon a thorough review of this specification will understand that the drainage rate should be optimized while also maintaining appropriate strength and flexibility of the stent 10 for usage within the desired body lumen.

While the filars 20 of the ureteral stent 10 may include many variations, such as dimensions, amount, and number of layers, the following example shown in FIG. 6 has been experimentally determined to provide adequate liquid flow through from the lumen of the stent and through the side walls of the stent while maintaining sufficient strength and flexibility for successful maintenance of patency through the ureter.

In some embodiments, the outer diameter 50 of the stent 10 may be about 0.072 inches while the inner diameter 52 of the stent 10, which corresponds to the lumen 18 diameter, may be about 0.044 inches. These dimensions allow the stent 10 to be used with a standard 0.038 inch guide wire. In some embodiments, the stent may be two layers of filars: an outer layer 54 made up of nine outer layer filars 58 and an inner layer 56 made up of nine inner layer filars 60. An exemplary outer layer filar 58 is shown in FIG. 7A, and an exemplary inner layer filar 60 is shown in FIG. 7B. Ideally, all nine of the inner layer filars 60 are identical in shape and size and all nine of the outer layer filars 58 are identical in shape and size. In this example, each outer layer filar 58 and inner layer filar 60 has a diameter of 0.007 inches. Further, in this embodiment, there may be pigtail loops on both the distal and proximal portions 12, 16 with diameters of around 1.5 centimeters.

The ureteral stent 10 described herein has various advantages over conventional plastic ureteral stent designs. As mentioned above, the need for drainage ports has been eliminated in the present design because the filars 20 allow for fluid to drain naturally from the lumen to a point external the patient along the entire length 9 of the stent. Additionally, the ureteral stent 10 has excellent tensile, torque, compressive, and radial force properties, thus ensuring the required strength to stabilize the ureter and maintain patency of the ureter and allow urine flow therethrough. However, despite the excellent strength properties of the ureteral stent 10, flexibility has not been sacrificed, thus ensuring minimal patient discomfort. Additionally, because the stent 10 includes openings at both ends of the lumen 18, the stent 10 may be fed over a guide wire during the insertion process. The stent 10 may also be made of a biocompatible metal that is corrosion resistant, thus allowing the stent 10 to remain in the patient for long periods of time before requiring replacement.

In use, to insert the ureteral stent 10 into a patient's ureter, a guide wire may first be provided. The guide wire may be inserted into a patient's ureter using conventional techniques. Next, the stent 10 may be advanced along the guide wire by inserting the guide wire into the lumen 18 of the stent 10. The stent 10 may be advanced into the patient's ureter until it is positioned at the desired location, such as spanning between the kidney and the bladder. Then, the guide wire may be removed from the patient's ureter, while the stent 10 remains in place. When no longer necessary or requiring replacement, the stent 10 may be removed from the patient's ureter through the use of a variety of well-known removal methods. Alternatively, the stent 10 may be inserted into the patient's ureter without the use of a guide wire.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A method for placing a stent, comprising:

providing a stent, the stent comprising a body extending between a distal end and a proximal end, the body defined by a plurality of elongated members, each elongated member extending between a distal end that is coterminous with the distal end of the body and a proximal end that is coterminous with the proximal end of the body, wherein each of the plurality of elongated members are arranged so as to define a lumen extending along the length of the plurality of elongated members, the lumen extending between the distal and proximal ends of the body so as to form a lumen length, wherein each of the plurality of elongated members are attached to adjacent elongated members at the distal end and proximal end forming continuous gaps between adjacent elongated members to permit drainage of a fluid from within the lumen through the gaps to an environment external the stent along the entire lumen length, wherein each of the plurality of elongated members are arranged so as to define a fixed outside diameter of the body; and advancing the stent into a patient until the stent is positioned within a clinically desired lumen within the patient, wherein the plurality of elongated members comprise a first plurality of elongated members and a second plurality of elongated members, wherein the first plurality of elongated members form an inner layer of the body to define the lumen, and the second plurality of elongated members form an outer layer of the body that surrounds the inner layer and each of the plurality of elongated members extend in a helical pattern to define a surface of the body and the lumen;

the first plurality of elongated members extend around and along the lumen in a clockwise helical pattern; and the second plurality of elongated members extend around and along the lumen in a counterclockwise helical pattern.

2. The method of claim 1, further comprising:

advancing a guide wire into the clinically desired lumen within the patient within the patient before the step of advancing the stent into the clinically desired lumen within the patient;

wherein the step of advancing the stent into the clinically desired lumen within the patient further comprising advancing the stent over the guide wire;

wherein the distal end of the body and the proximal end of the body are polished so as to ease advancement of the stent.

3. The method of claim 2, further comprising:

removing the guide wire from the patient.

4. The method of claim 1, further comprising:

removing the stent from the patient.

5. The method of claim 1, wherein:

the gaps between the adjacent elongated members extend continuously from the distal end of the body to the proximal end of the body.

\* \* \* \* \*